United States Patent
Pierce et al.

(10) Patent No.: US 8,568,257 B2
(45) Date of Patent: Oct. 29, 2013

(54) FRANGIBLE PAYLOAD DELIVERY APPARATUS

(75) Inventors: William Fred Pierce, DeQuincy, LA (US); Tony James Laitiolais, St. Martinville, LA (US)

(73) Assignee: Rac Em Bac, L.L.C., DeQuincy, LA (US)

( * ) Notice: Subject to any disclaimer, the term of this patent is extended or adjusted under 35 U.S.C. 154(b) by 0 days.

(21) Appl. No.: 13/488,684

(22) Filed: Jun. 5, 2012

(65) Prior Publication Data

US 2013/0065716 A1 Mar. 14, 2013

Related U.S. Application Data

(63) Continuation-in-part of application No. 13/199,901, filed on Sep. 13, 2011, now Pat. No. 8,444,512.

(51) Int. Cl.
*F42B 6/08* (2006.01)

(52) U.S. Cl.
USPC ........................................... 473/581; 473/583

(58) Field of Classification Search
USPC .......................... 473/578, 581, 582, 583, 584
See application file for complete search history.

(56) References Cited

U.S. PATENT DOCUMENTS

| | | | |
|---|---|---|---|
| 4,726,584 A | 2/1988 | Bishop | |
| 5,836,842 A | 11/1998 | McLearan | |
| 6,450,905 B1 | 9/2002 | Edlund | |
| 2008/0051231 A1 | 2/2008 | Everett | |

*Primary Examiner* — John Ricci
(74) *Attorney, Agent, or Firm* — Schultz & Associates, P.C.

(57) ABSTRACT

A payload delivery apparatus comprised of a frangible hollow body for delivering a variety of payloads. The body is attached to a base having a threaded section for removable engagement with an arrow shaft. A plurality of equidistant spaced impact stanchions are attached around the perimeter of the body. A cap is fitted to an open end of the hollow body. Each impact stanchion is connected to the hollow body in such a way as to fracture upon impact with a target thus delivering the payload. In an alternate embodiment, a set of aerodynamic linear channels and annular indentions is included in the body so as to aid to fracturing upon impact.

32 Claims, 7 Drawing Sheets

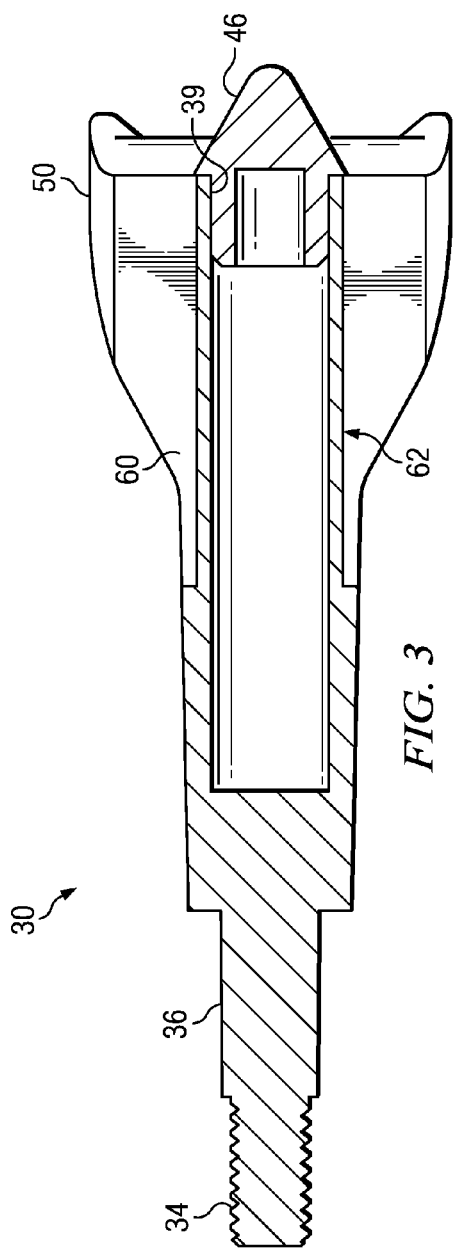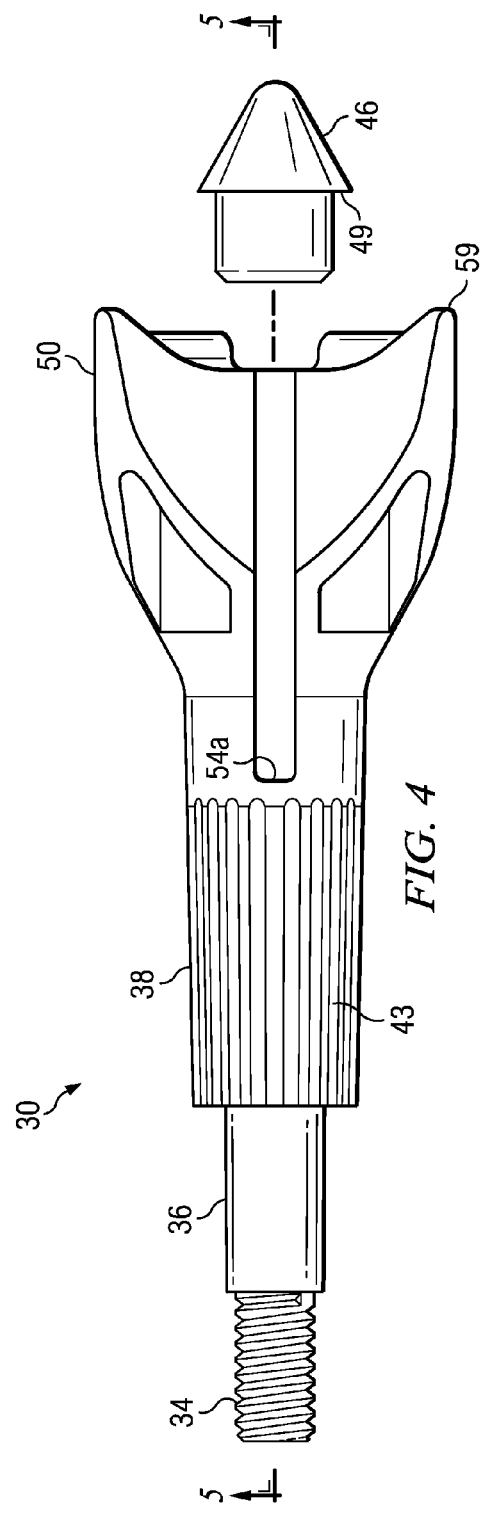

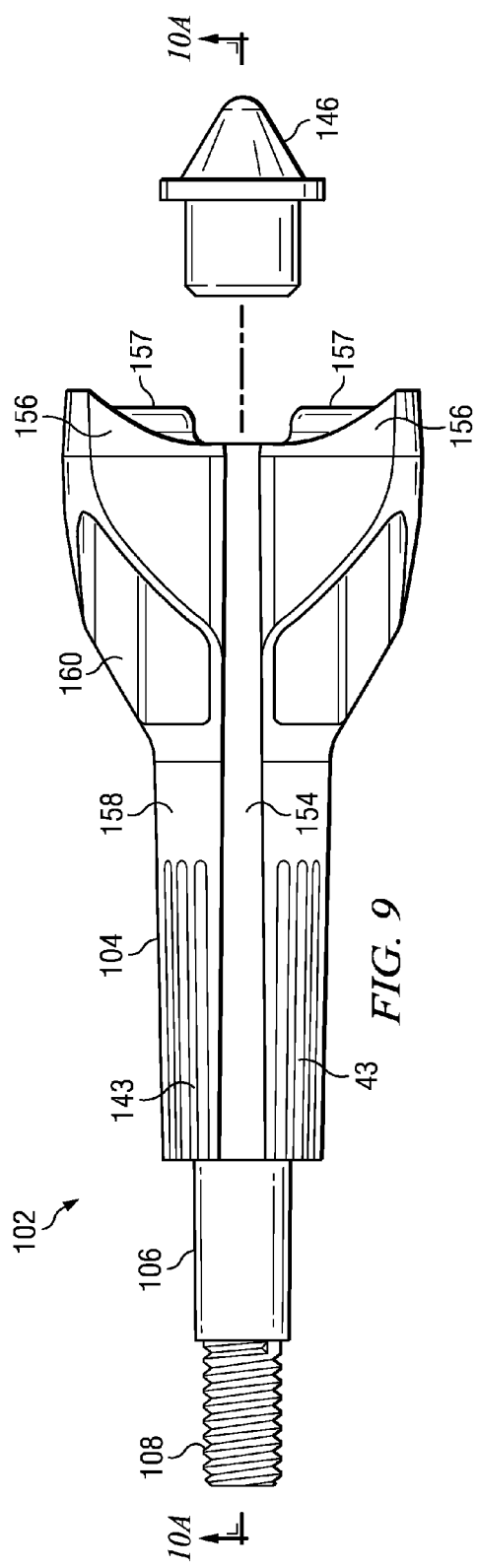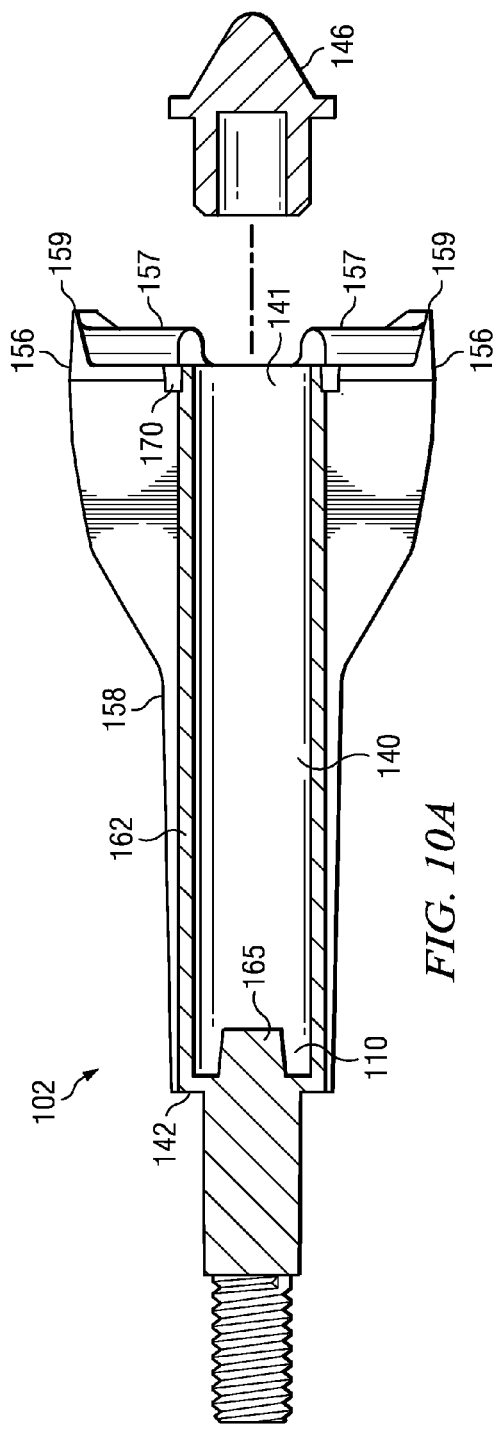
FIG. 9
FIG. 10A

FRANGIBLE PAYLOAD DELIVERY APPARATUS

CROSS-REFERENCE TO RELATED APPLICATIONS

This application is a Continuation-in-Part claiming priority benefit from U.S. patent application Ser. No. 13/199,901 filed Sep. 13, 2011 now U.S. Pat. No. 8,444,512, which claims priority benefit from U.S. patent application Ser. No. 12/928,772 filed on Dec. 16, 2010.

BACKGROUND OF THE INVENTION

This disclosure relates to hunting equipment, and more particularly to an arrow which is capable of disposably transporting a payload to a target.

In the sport of game hunting it is conventional for a hunter to select a spot believed to be in a path or other area where the game is likely to be and wait for the animal in a tree or other hiding place. Typically, a hunting stand is erected on a tree above the expected travel path of the animals where a hunter can stay without searing the animal and without leaving a human scent. To improve the hunter's odds, an attractant such as the scent of such animal may be left in the area so that other animals of the species would investigate it and while doing so, offer more target opportunities for the hunter.

Furthermore, the hunter hiding in a tree has to descend to the ground and spread the scent manually in the target area. A conventional alternative was to wet a rag or other absorbent material, tie the rag to an arrow and then fire the arrow from the tree stand. However, such approach suffers from major disadvantages. For example, the liquid can be spilled on the hunter or his clothes. Moreover, some of the scent is dispersed during the arrow flight and very little of the liquid reaches the ground.

My co-pending application discloses an improved scent dispersing arrowhead where a hollow body has a pair of opposing cutouts through which an animal attractant, such as liquid scent can exit the hollow body. The hollow body is configured to retain a frangible liquid-scent containing capsule. A plunger is configured to slide into the scent capsule enclosure and cause rapture the scent-containing capsule upon impact of the plunger with a solid surface, such as ground, rock or tree limb. While this arrowhead has distinct advantages over conventional scent dispersing arrows, it was discovered that a narrow forward tip of the arrowhead tends to at least slightly penetrate the soil and thus disperse a portion of the scent liquid into the soil.

For example, U.S. Pat. No. 6,450,905 to Edlund, discloses a scent dispersion arrow including an active arrow tip which uses a compression fitting to attach to an out shaft. A scent dispersion head, containing a sponge holding a liquid scent had a cavity in the arrow tip. The cavity is sealed against the compression fittings. When deployed, the arrow tip advances in the cavity dispersing the scent through openings in the arrowhead.

As another example, U.S. Pat. No. 5,836,842 to McLearan, discloses an arrow for dispersing a scent with an active arrowhead. The arrowhead is blunt and includes a deployment orifice connected to a rigid tube. A scent is contained in the arrow body in a container which is sealed around the tube. Upon impact, the arrow body drives the container along the tube thereby forcing the scent liquid through the tube and out of the orifice to be deployed at the target.

As another example, U.S. Pat. No. 4,726,584 to Bishop, discloses a scent releasing arrow which includes a hollow tubular metal shaft having a pad of absorbent material located within it. It's adjacent a group of openings. A cylindrical sleeve covers the openings until the arrow is deployed. Upon deployment the cover slides forward uncovering the holes and releasing the scent.

Similarly, United States Patent Publication No. 2008/0051231A1 to Everett, discloses a hollow scent arrow having a plurality of holes. The hollow arrow includes a wick stick adjacent the holes filled the scent liquid. Also within the hollow arrow is a heavy slug which is free to slide within the arrow compartment behind the wick stick. Upon deployment, the slug advances pressing the wick stick and releasing the scent out of the holes.

SUMMARY

This disclosure provides, in one preferred embodiment, a scent dispersing apparatus including a scent dispersing assembly configured for attachment to an arrow that can be fired from a tree stand or other concealed area in a hunting position.

A preferred embodiment includes a frangible hollow housing defining a liquid-scent enclosure. The housing has a generally cylindrical hollow body and a plurality of fins secured about an outer periphery of the hollow body and extending outwardly therefrom. The fins resemble buttresses secured to a forward end of the housing. The fins are adapted to substantially increase outer dimensions of a forward end of the housing and prevent the housing from being embedded into the soil upon impact. The hollow body is configured to fracture upon impact with a solid surface releasing the liquid animal attractant.

Another preferred embodiment includes a payload of #20 birdshot.

Another preferred embodiment includes a payload of a tracking module and an antenna.

Yet another preferred embodiment includes a payload of paint, medicine or pesticide.

BRIEF DESCRIPTION OF THE DRAWINGS

Reference will now be made to the drawings, wherein like parts are designated by like numerals, and wherein

FIG. 3 is a sectional view of the scent dispersing arrow of this disclosure.

FIG. 4 is an elevation view of the scent dispersing arrow of this disclosure, with the cap detached.

FIG. 9 is an elevation view of an alternate preferred embodiment of a payload delivery apparatus, with the cap detached.

FIG. 10A is a sectional view of an alternate preferred embodiment of a payload delivery apparatus taken along line 10A-10A of FIG. 9.

DETAILED DESCRIPTION

Figures 2, 6:
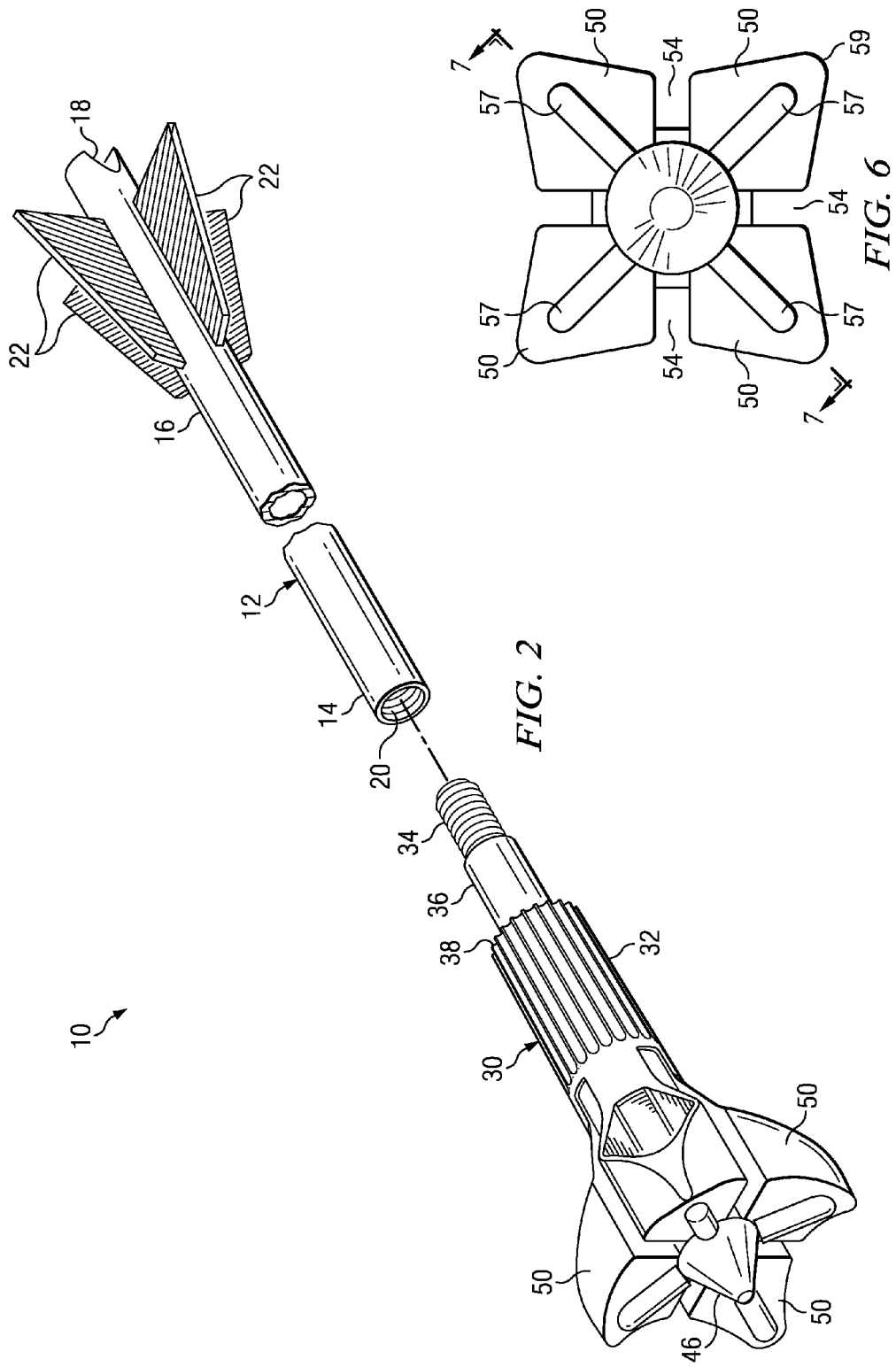
FIG. 2 is a perspective view of the scent dispersing arrow of this disclosure.
FIG. 6 is an end view of the scent dispersing arrow of this disclosure.
Figure 5:
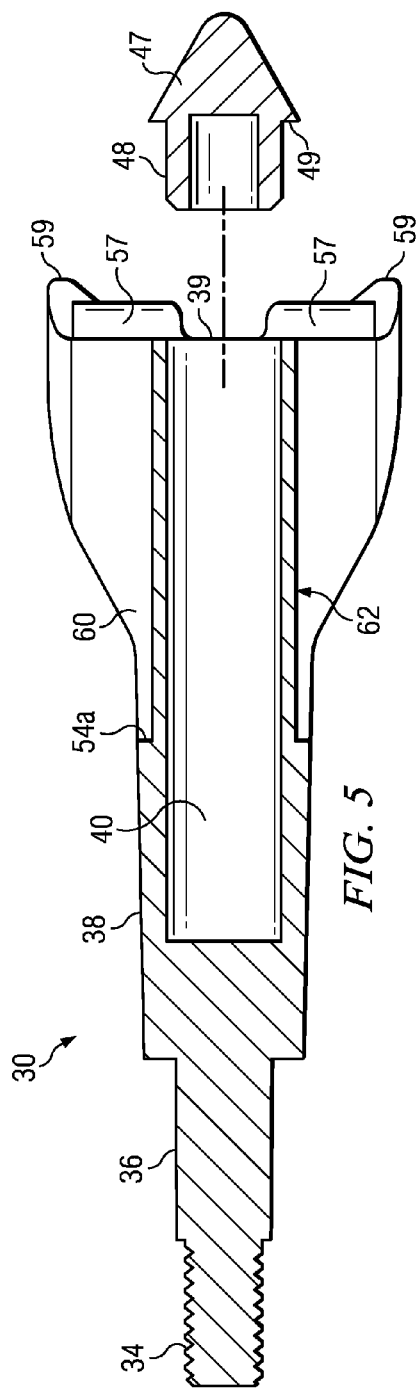
FIG. 5 is a sectional view taken along line 5-5 of FIG. 4.
Figure 7:
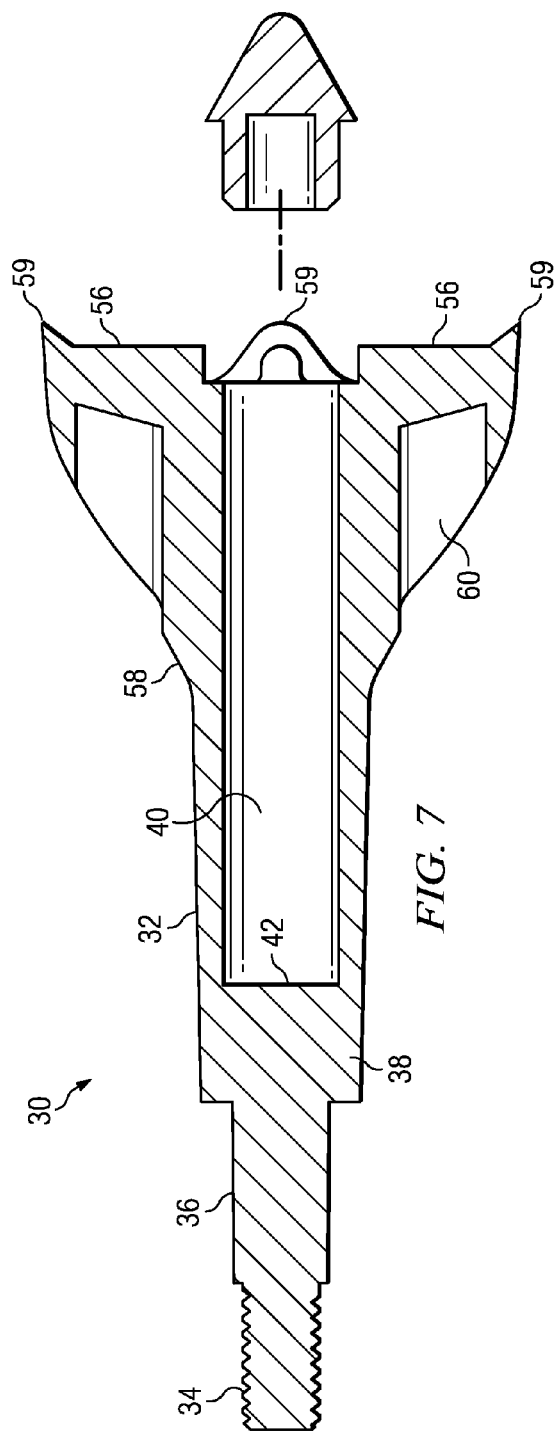
FIG. 7 is a sectional view taken along line 7-7 of FIG. 6.

Turning now to FIG. 2, arrow 10 designates the scent dispersing arrow in accordance with the present disclosure. Arrow 10 comprises an elongated cylindrical arrow shaft 12. Arrow shaft 12 has open forward end 14 and closed distant end 16. Nock 18 is formed in distant end 16 to accommodate a bow string. Forward end 14 of shaft 12 is open and threaded insert 20 is positioned therein. Conventional vanes 22 may be attached to arrow shaft 12 adjacent distant end 16. Arrow 10 may have multiple vanes 22 equidistantly spaced about the circumference of arrow shaft 12.

Scent dispersing assembly 30 is detachably secured on arrow shaft 12. The scent dispersing assembly comprises housing 32 having proximate threaded portion 34. The threads of the proximate portion are configured to matingly detachably engage with the threads of insert 20. Housing 32 also comprises intermediate portion 36, which can be formed as a cylindrical member, as a transitional member between proximate threaded portion 34 and distant portion 38.

Distant portion 38 is formed as a generally cylindrical hollow member having a diameter greater than threaded portion 34 and intermediate portion 36. Of course, housing 32 can be formed as a cylindrical body having the same diameter from one end to the other, with one end having external threads similar to the threads-threaded portion 34. If desired, the exterior surface of the distant portion provided with plurality of ridges 43, which increase friction or the exterior surface and facilitate a better grip of the scent dispersing assembly by a user. This feature is particularly beneficial when the user threadably engages the scent dispersing assembly with arrow shaft 12.

Referring to FIGS. 3, 4, 5, and 7, in one aspect of the disclosure, distant portion 38 defines internal chamber 40, which extends through a major part of distant portion 38. Distant portion 38 has open end 39 opposite threaded portion 34. Opposite open end 39, chamber 40 is closed by transverse inner wall 42. It is envisioned that chamber 40 is sized to retain about 100 mg of synthetic or natural scent that is designed to attract animals being hunted during a particular hunting season.

Detachable cap 46 is configured to close open end 39 after a scented liquid is loaded into chamber 40. Cap 46 has generally conical first part 47 and generally cylindrical second part 48. Second part 48 of cap 46 can be made hollow. The exterior dimensions of second part 48 are such that second part 48 frictionally engages interior sidewall of chamber 40, fitting into open end 39 when cap 46 is engaged with open end 39 of distant portion 38. Shoulder 49 formed between first part 47 and second part 48 of cap 46. Shoulder 49 engages outer end 39 of distant portion 38 when the cap is fitted into the opening of end 39.

Referring to FIG. 6, plurality of fins 50 is equidistantly secured about a forward part 52 of the distant portion 38. Fins 50 resemble buttresses surrounding the cylindrical distant portion 38. Fins 50 are separated by channels 54 which are designed to improve aerodynamics and fracturing characteristics of arrow 10. In a preferred embodiment, channels 54 are approximately 0.984" (2.5 cm) in length. The channels terminate at channel ends Ma. Each channel end further serves as a stress riser which aids in fracturing the housing upon impact. As can be seen in the drawings, fins 50 substantially increase the outer dimensions of distant end 38. In one aspect of the disclosure, each fin 50 has an outwardly flaring end plate 56 unitary formed with attachment member 58, which secures fin 50 to the exterior of distant portion 38. The flaring plate includes support flange 57 which serves to strengthen the end plate and the fin so that upon impact the force from the end plate is transmitted to the channels and the stress risers. End plate 56 is provided with talon 59 that extends as the most forward point of housing 32. Support flange 57 begins at end 39 and extends to talon 59. The talons serve to increase the ability of the fin to grip the impact surface and not be deflected.

Referring to FIGS. 3, 4, 5, and 7, fin 50 may be formed hollow as a shell or with open proximate end 60. Proximate end 60 is formed opposite end plate 56 of fin 50. In one aspect of the disclosure, combined surface area of end plates 56 is almost twice as large as the diameter of the cylindrical distant portion 38 without fins 50. Fins 50 can be triangular in cross-section or resemble a rhombus. Although four such fins are shown in the drawings, it will be realized that other numbers of fins can be used as well.

Distant portion 38 is formed as a thin-walled enclosure for the scent dispersing liquid that is loaded into chamber 40. In one of the preferred embodiments cylindrical wall 62 is about 0.03" (0.761 mm) thick to encourage distant portion 38 to fracture upon impact with a solid surface, such as the ground or a tree trunk. The diameter of chamber 40 can be about 0.25" (6.35 mm). The distance between a pair of opposing talons 59 of fins 50 can be about 1" (25.4 mm); the length of the scent dispersing assembly can be about 2.38" (60.45 mm); and the length of distant portion 38 can be about 1.7" (43.18 mm). Of course, these dimensions are exemplary and other dimensions will suffice.

Scent dispersing assembly 30 can be made from a variety of frangible materials, such as for instance thin plastic. In one preferred embodiment, the plastic is a polyolefin, namely, a polypropylene homopolymer. The arrow shaft can be made of rigid plastic or other conventional material. It is envisioned that scent dispersing assembly 30 can be manufactured and sold separately from arrow 12, and be adapted for use with any type of arrow. A kit containing a plurality of the scent dispersing assemblies 30 can be sold as a separate item.

Figure 1:
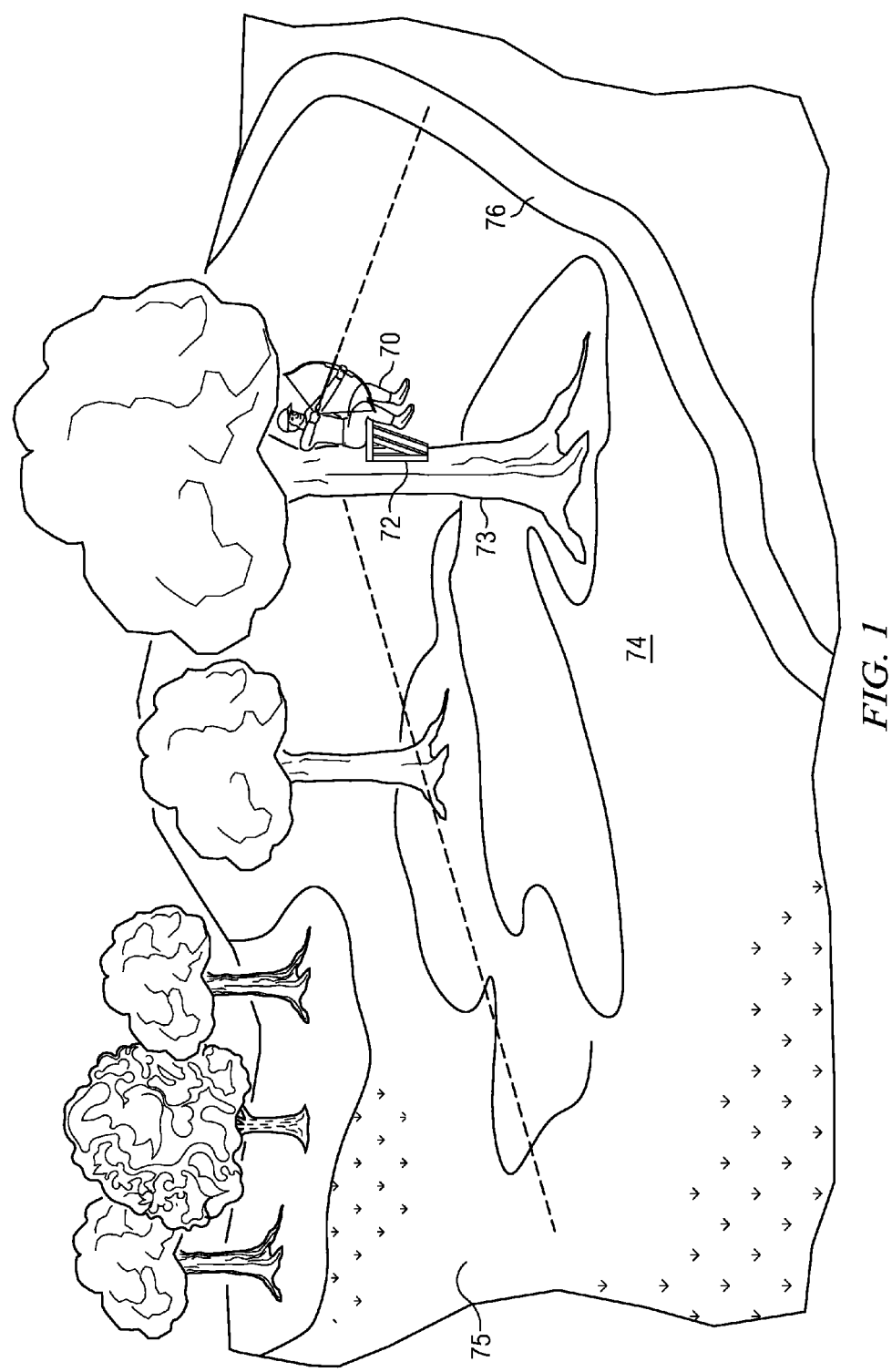
FIG. 1 is a schematic view of the hunting location where the scent dispersing arrow of this disclosure is used.

Referring to FIG. 1, in operation, hunter 70 is positioned in tree stand 72, which is elevated above ground 74. Usually, tree stand 72 is erected in a location adjacent food plot 75 or trail 76 frequented by the animals, such as deer. Preferably, the area around tree 73 where the tree stand is positioned contains minimal human scent that can be discerned by the hunted animal.

Hunter 70 selects one scent dispersing assembly 30, which has been pre-loaded with the desired scent in chamber 40. Chamber 40 is closed with cap 46. The hunter then threadably engages scent dispersing assembly 30 with arrow shaft 12 using matching threads 20 in shaft 12 and the external threads on threaded portion 34. Once scent dispersing assembly 30 is securely engaged with arrow shaft 12, the hunter fires the arrow aiming either toward food plot 75 or to trail 76. The trajectory of the arrow flight is shown in phantom lines.

As the arrow hits ground 74 wide end plates 56 of fins 50 prevent the scent dispersing assembly 30 from embedding in the soil. Talons 59 of fins 50 can impact the target. The impact force, made stronger by the weight of the liquid in chamber 40 and fins 50 is transmitted to the body of distant portion 38.

Figure 8:
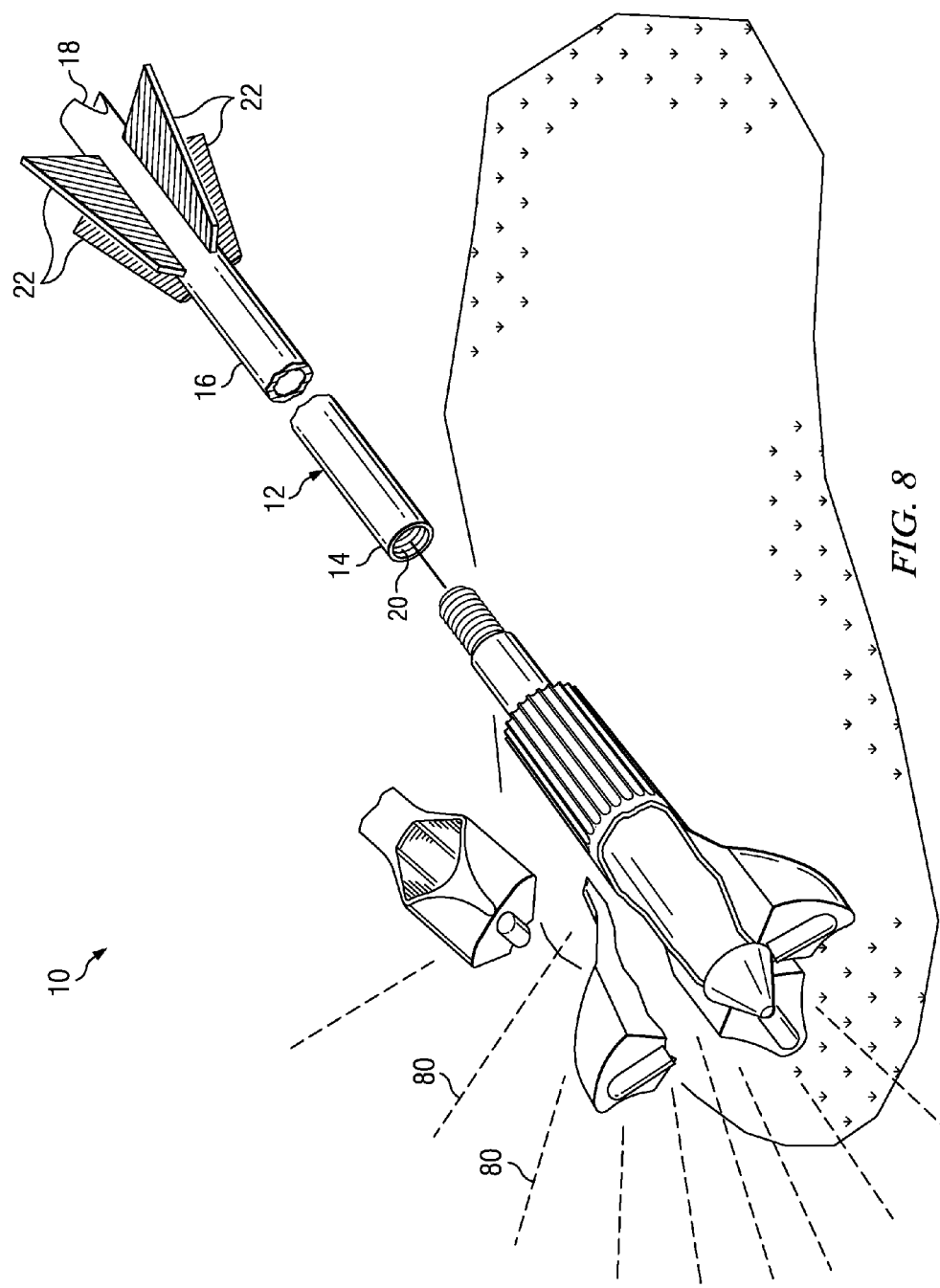
FIG. 8 illustrates the scent dispensing arrow broken upon impact with the ground.

Referring to FIG. 8, the forceful impact of the fins with a solid surface transmits the impact force to housing 32 and down channels 54 to channel ends 54a, causing the thin walls to fracture and disperse the liquid in the area of the impact. As a consequence, the liquid scent exits the housing 32 in a "fan-like" fashion, as illustrated in phantom lines 80. Following the hunt, hunter 70 can retrieve the arrow, disengage the broken housing 32 from arrow shaft 12 and engage another assembly 30 with liquid scent with shaft 12. Arrow shaft 12 can thus be used numerous times.

In one alternative embodiment, the present disclosure prevent spills of the liquid scent on the hunter or hunter's closing by using an encapsulated item. The hunter can select the most advantageous point for scent dispersal from an elevated position, without leaving undesirable human scent on the deer trail. The targeted delivery of the liquid scent to the most desired area ensures maximum exposure thereof to the game.

Figure 10B:
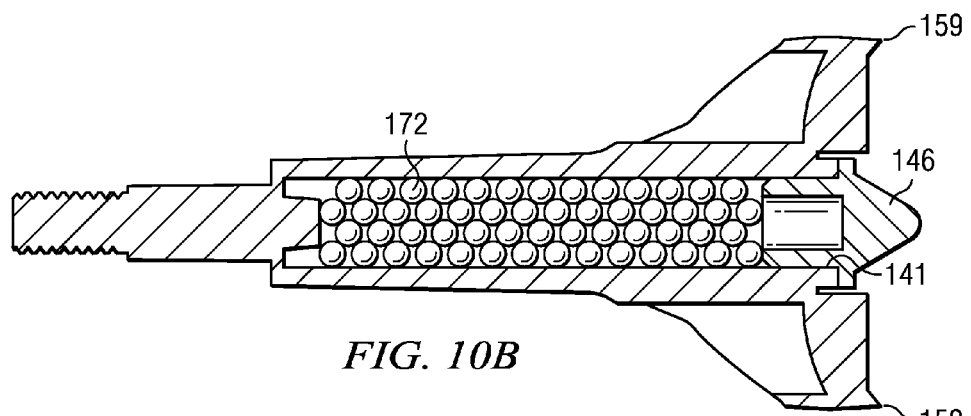
FIG. 10B is a sectional view of an alternate preferred embodiment of a payload delivery apparatus showing a shot payload taken along 10B-10B of FIG. 11.

Referring to FIGS. 9 and 10A-B, an alternate preferred embodiment is shown. Payload delivery apparatus 102 is comprised of a frangible hollow nacelle 104 integrally formed with base 106. The preferred embodiment of payload delivery apparatus 102 is manufactured from a class of polyolefin known for its rigid characteristics, such as a polypropylene homopolymer. Other generally rigid plastics or ceramic materials should suffice. Both nacelle 104 and base 106 are generally cylindrical in shape. Base 106 includes threaded portion 108 having external threads sized to engage the internal threads of insert 20 of arrow shaft 12. Nacelle 104 is connected to base 106 by transverse inner wall 142. Cylindrical wall 162 forms chamber 140. Transverse inner wall 142 encloses chamber 140 proximate base 106. Payload driver 165 extends from transverse inner wall 142 into chamber 140. Payload driver 165 is generally conical or frusto-conical in shape. Stress riser 110 forms a circular ring around payload driver 165 which reduces the strength of the nacelle and forms a break point.

Chamber 140 terminates with hole 141. Hole 141 frictionally receives cap 146. Nacelle 104 further includes a plurality of raised attachment members 158 to which are attached a plurality of impact stanchions 150. Attachment members 158 each include a plurality of slots 143. Slots 143 are aligned parallel to the central axis of nacelle 104 and function to reduce weight of the nacelle and aid in gripping while threading the threaded portion onto an arrow shaft.

Figure 11:
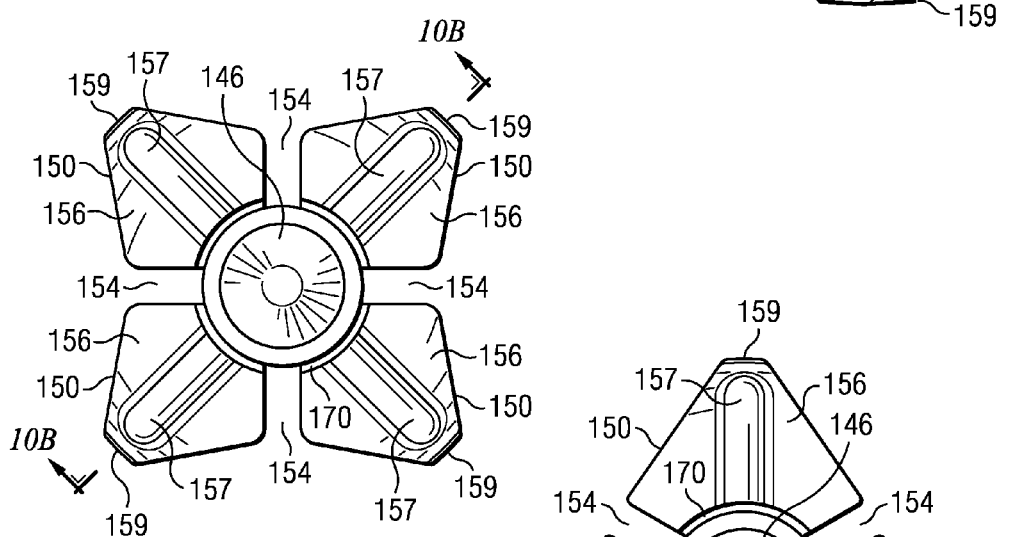
FIG. 11 is an end view of an alternate preferred embodiment of a payload delivering apparatus showing four impact stanchions.
Figure 12:
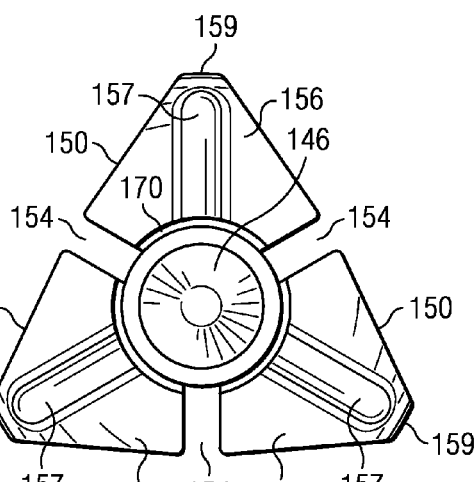
FIG. 12 is an end view of an alternate preferred embodiment of a payload delivering apparatus showing three impact stanchions.
Figure 13:
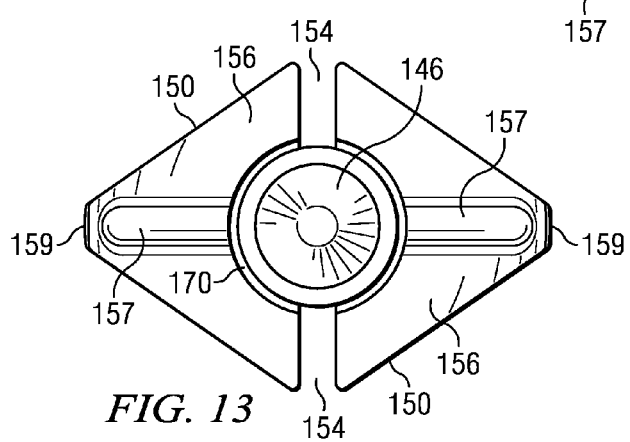
FIG. 13 is an end view of an alternate preferred embodiment of a payload delivering apparatus showing two impact stanchions.

FIGS. 11, 12 and 13 show different preferred embodiments of the nacelle. Impact stanchions 150 are spaced equidistantly and symmetrically around the perimeter of the nacelle. The number of impact stanchions may vary. Although two, three, and four impact stanchions have been depicted, it is within the scope of the disclosure to have as many stanchions as is required for any particular payload delivery scenario. Each impact stanchion 150 is integrally formed with its respective attachment member 158. Impact stanchions 150 and attachment members 158 are separated by channels 154. Channels 154 traverse the length of the hollow nacelle longitudinally. The channels reduce the thickness of the walls of chamber 140 to between about 0.025" and about 0.035".

Referring again to FIG. 9, each impact stanchion 150 has an outwardly flaring endplate 156. Each impact stanchion 150 may be enclosed and hollow or include an open end 160. Each endplate 156 is separated from cylindrical wall 162 by stress riser 170. Each endplate 156 is provided with support flange 157 originating at stress riser 170 and culminating at talon 159. Each talon extends forward of the nacelle. Stress risers 110 and 170 and channels 154 cooperate to provide predetermined break lines for the nacelle upon impact with an intended target.

The overall size of payload delivery apparatus 102 will vary with the size and requirement of the desired payload to be delivered. It is expected that payload delivery apparatus 102 may be used with solid payloads and liquid payloads. Referring to FIG. 10B, one example of a payload includes #20 bird shot. In this embodiment, #20 bird shot is packed into the nacelle and secured with cap 146. In other embodiments, pellets of differing sizes, weights and compositions may be employed. A singular metal or plastic projectile, paint balls, animal attractants, and tranquilizers may also be used as payloads. Additional payloads include narcotics, poisons, medicines, and human or animal scent or remains for training dogs or forensic investigators. Agricultural applications are envisioned where the payload may include seeds, fungicides and/or pesticides. Many applications are also possible utilizing liquid paint as the payload, preferably iridescent or ultraviolet paints.

In use, the preloaded nacelle is attached to the shaft of an arrow by engaging threaded portion 108 with the internal threads of insert 20 on arrow shaft 12. If the nacelle is not preloaded, cap 146 is removed from nacelle 104, desired payload 172 is loaded into chamber 140, and cap 146 is frictionally reinserted into place enclosing the payload in chamber 140. The nacelle is then deployed using a bow or crossbow, as known in the art, at the intended target.

As the nacelle hits the target, it fails at stress risers 110 and 170 and channels 154 and shatters. Impact stanchions 150 break away from nacelle 104. Nacelle 104 breaks away from base 106. The momentum of arrow 10 pushes base 106 and payload driver 165 through payload 172, spreading payload 172 out at the intended target. Arrow 10 may be retrieved and re-used.

In the case of bird shot as a payload, an unexpected result was achieved. Extremely high penetration rates were achieved with repeated tests on chicken and turkey carcasses. The tests showed conclusively that the delivery pattern of #20 bird shot resulting from delivery with the nacelle was between about 0.5" and 1.5" with complete penetration. It is postulated that the small pattern was achieved because of the function of the nacelle in containing dispersion of the bird shot until impact with the target. It is further postulated that the good penetration was aided by the impact driver.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the appended claims.

The invention claimed is:

1. An arrowhead comprising:
    a body having a longitudinal axis;
    a sealable internal chamber in the body;
    a set of frangible stanchions attached to the body adjacent the sealable internal chamber;
    an outwardly flaring plate, generally perpendicular to the longitudinal axis, attached to each frangible stanchion of the set of frangible stanchions.

2. The arrowhead of claim 1 wherein the set of frangible stanchions is attached to the body in a symmetrical pattern.

3. The arrowhead of claim 2 wherein the set of frangible stanchions includes four (4) frangible stanchions.

4. The arrowhead of claim 1 wherein each frangible stanchion is hollow.

5. The arrowhead of claim 1 wherein each frangible stanchion of the set of frangible stanchions is separated by a longitudinal aerodynamic stress riser.

6. The arrowhead of claim 1 further comprising a forward facing cap, affixed in the sealable internal chamber, coaxial with the longitudinal axis.

7. The arrowhead of claim 6 further comprising a generally circular stress riser between the forward facing cap and the set of frangible stanchions.

8. The arrowhead of claim 1 further comprising peripheral talon attached to the outwardly flaring plate.

9. The arrowhead of claim 8 further comprising radial reinforcing ball integrally formed with the outwardly flaring plate and the peripheral talon.

10. The arrowhead of claim 1 further comprising an impact driver at a base of the internal chamber, coaxial with the longitudinal axis.

11. The arrowhead of claim 10 wherein the impact driver is separated from an interior wall of the internal chamber by a generally circular stress riser.

12. The arrowhead of claim 1 further comprising a payload in the internal chamber.

13. The arrowhead of claim 12 wherein the payload is a particulate.

14. The arrowhead of claim 13 wherein the particulate is birdshot.

15. The arrowhead of claim 12 wherein the payload is a scented liquid.

16. The arrowhead of claim 12 wherein the payload is an animal attractant.

17. The arrowhead of claim 12 wherein the payload is one of the group of bird shot, pellets, a projectile, paint, a tranquilizer, narcotics, a scented material, seeds, fungicides, a poison, or a pesticide.

18. The arrowhead of claim 1 further comprising an attachment means, attached to the body, for connection to an arrow shaft.

19. The arrowhead of claim 1 wherein the body is generally cylindrical and has a wall thickness of between about 0.025 inches and about 0.035 inches.

20. The arrowhead of claim 1 wherein the body is comprised of the plastic is a polyolefin, namely, a polypropylene homopolymer.

21. A payload delivery apparatus for attachment to an arrow shaft to deliver a payload to a target, the payload delivery apparatus comprising:
a nacelle, having a generally cylindrical body, connected to a generally cylindrical base;
the base having a threaded section for threadably engaging the arrow shaft;
the nacelle having a cylindrical wall forming an interior chamber, where the interior chamber has a closed end and an open end;
the closed end having a first stress riser surrounding a payload driver extending from the base into the interior chamber;
a set of impact stanchions integrally formed with the cylindrical wall and spaced equidistantly around the nacelle, wherein the impact stanchions are separated by a set of aerodynamic fracture channels;
a second stress riser, adjacent the open end, and between each impact stanchion of the set of impact stanchions and the nacelle; and
each impact stanchion of the set of impact stanchions further comprising an outwardly flaring endplate, wherein each endplate includes a support flange extending from the second stress riser to a point extending forward of the nacelle.

22. The payload delivery apparatus of claim 21 further comprising:
a detachable cap adjacent the cylindrical wall and seated in the open end.

23. The payload delivery apparatus of claim 21 wherein the first stress riser further comprises a circular ring between the nacelle and the base.

24. The payload delivery apparatus of claim 21 further comprising:
wherein the first stress riser, the second stress riser, and the channels form a set of break points in the nacelle.

25. The payload delivery apparatus of claim 21 wherein the payload contained in the interior chamber consists of one or more of the group of: bird shot, pellets, a singular projectile, paint balls, animal attractants, a tranquilizer, narcotics, human scent, animal scent, seeds, fungicides, pesticides, and liquid paint.

26. The payload delivery apparatus of claim 21 where the nacelle includes a plurality of gripping slots aligned parallel to a longitudinal axis of the nacelle.

27. The payload delivery apparatus of claim 21, wherein the thickness of the cylindrical wall is reduced by the set of aerodynamic fracture channels to a thickness in the range of about 0.025 inches to about 0.035 inches.

28. The payload delivery apparatus of claim 21, wherein the set of impact stanchions comprises of one of the group: of two impact stanchions, three impact stanchions, and four impact stanchions.

29. A method of delivering a payload with an arrow having a longitudinal axis comprising the steps of:
attaching a frangible arrowhead, having a payload in a body with a hollow internal chamber and a set of planar outwardly flaring talons generally perpendicular to the longitudinal axis to the arrow;
deploying the arrow and the frangible arrowhead at a target; and
fracturing the body by impacting the flaring talons on the target thereby delivering the payload.

30. The method of claim 29 further comprising the step of:
inserting the payload in the hollow internal chamber.

31. The method of claim 29 further comprising the steps of:
providing an impact driver at a base of the hollow internal chamber; and,
driving the payload into the target with the impact driver.

32. The method of claim 29 further comprising the steps of:
providing a plurality of stress risers on the body adjacent the hollow internal chamber; and,
wherein the step of fracturing further comprises:
fracturing the body at one or more of the plurality of stress risers.

* * * * *